United States Patent [19]

Krüger et al.

[11] Patent Number: 4,601,748
[45] Date of Patent: Jul. 22, 1986

[54] 2-PHENOXY PROPIONIC ACID DERIVATIVES OF PENTITE, PROCESS FOR THE PRODUCTION OF THESE COMPOUNDS AS WELL AS COMPOSITIONS CONTAINING THE SAME HAVING HERBICIDAL EFFECTIVENESS

[75] Inventors: Hans-Rudolf Krüger; Friedrich Arndt, both of Berlin, Fed. Rep. of Germany

[73] Assignee: Schering Aktiengesellschaft, Berlin and Bergkamen, Fed. Rep. of Germany

[21] Appl. No.: 540,611

[22] Filed: Oct. 7, 1983

[30] Foreign Application Priority Data

Oct. 19, 1982 [DE] Fed. Rep. of Germany ....... 3239035

[51] Int. Cl.[4] .................. C07D 213/64; A01N 43/40
[52] U.S. Cl. ........................................ 71/94; 546/283; 544/354; 549/448
[58] Field of Search ............................ 546/283; 71/94

[56] References Cited

PUBLICATIONS

Paerels et al., Chemical Abstracts, vol. 99, (25), Abst. No. 212,909x, Dec. 19, 1983.

*Primary Examiner*—Alan L. Rotman
*Attorney, Agent, or Firm*—Michael J. Striker

[57] ABSTRACT

New 2-phenoxy propionic acid derivatives of pentite are disclosed, of the general Formula

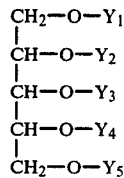

in which one of the substituents Y is the group

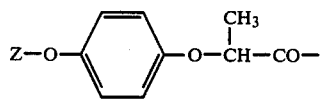

and pairs of other substituents Y are the group

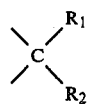

wherein
Z is phenyl, 2-pyridyl, or 2-quinoxalinyl, or phenyl, 2-pyridyl or 2-quinoxalinyl substituted one or more times the same or differently by halogen, $C_1$-$C_6$-alkoxy, $C_1$-$C_6$-alkyl, nitro or trifluoromethyl and
$R_1$ and $R_2$ are the same or different and are each hydrogen, $C_1$-$C_{10}$-alkyl, $C_1$-$C_{10}$-alkyl substituted one or more times the same or differently by halogen, $C_1$-$C_6$-alkoxy, phenoxy or halogen phenoxy, aryl-$C_1$-$C_3$-alkyl, aryl-$C_1$-$C_3$-alkyl substituted one or more times the same or differently by $C_1$-$C_6$-alkyl, halogen, $C_1$-$C_6$-alkoxy, nitro or trifluoromethyl, $C_3$-$C_6$-cycloaliphatic hydrocarbon, aromatic hydrocarbon or aromatic hydrocarbon substituted one or more times the same or differently by $C_1$-$C_6$-alkyl, halogen, $C_1$-$C_6$-alkoxy, nitro or trifluoromethyl,
or $R_1$ and $R_2$ together with the C-atom to which they are both bonded are a $C_3$-$C_8$-cycloaliphatic hydrocarbon,
along with processes for the production of these compounds as well as compositions containing the same and having herbicidal effectiveness.

14 Claims, No Drawings

2-PHENOXY PROPIONIC ACID DERIVATIVES OF PENTITE, PROCESS FOR THE PRODUCTION OF THESE COMPOUNDS AS WELL AS COMPOSITIONS CONTAINING THE SAME HAVING HERBICIDAL EFFECTIVENESS

BACKGROUND OF THE INVENTION

The invention concerns new 2-phenoxy propionic acid derivatives of pentite, processes for the production of these compounds as well as compositions containing the same having herbicidal effectiveness.

Propionic acid derivatives of pentite having biological effectiveness have not previously been known.

It is therefore an object of the present invention to provide new active substances having more advantageous herbicidal activity.

SUMMARY OF THE INVENTION

This object is attained according to the present invention by a composition which contains as active substance at least one 2-phenoxy propionic acid derivative of pentite of the Formula

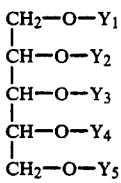

I in which one of the substituents Y is the group

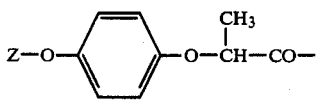

and pairs of other substituents Y are the group

wherein

Z is phenyl, 2-pyridyl or 2-quinoxalinyl, or phenyl, 2-pyridyl or 2-quinoxalinyl substituted one or more times the same or differently by halogen, $C_1$–$C_6$-alkoxy, $C_1$–$C_6$-alkyl, nitro or trifluoromethyl and $R_1$ and $R_2$ are the same or different and are each hydrogen, $C_1$–$C_{10}$-alkyl, $C_1$–$C_{10}$-alkyl substituted one or more times the same or differently by halogen, $C_1$–$C_6$-alkoxy, phenoxy or halogen phenoxy, aryl-$C_1$–$C_3$-alkyl, aryl-$C_1$–$C_3$-alkyl substituted one or more times the same or differently by $C_1$–$C_6$-alkyl, halogen, $C_1$–$C_6$-alkoxy, nitro or trifluoromethyl, $C_3$–$C_6$-cycloaliphatic hydrocarbon, aromatic hydrocarbon or aromatic hydrocarbon substituted one or more times the same or differently by $C_1$–$C_6$-alkyl, halogen, $C_1$–$C_6$-alkoxy, nitro or trifluoromethyl, or $R_1$ and $R_2$ together with the C-atom to which they are both bonded are a $C_3$–$C_8$-cycloaliphatic hydrocarbon.

The compositions according to the present invention are suitable in surprising manner for the control of weeds, even while sparing the culture plants, and therefore considerably enrich the state of the art in this field.

The compositions according to the present invention are useful, for example, for selective combating of difficult to fight weed grasses, such as *Avena fatua*, *Alopecurus myosuroides*, Echinochloa c.g., Setaria sp., *Setaria faberi*, *Digitaria sanguinalis*, *Sorghum halepense*, *Poa annua*, Bromus sp. *Agropyron repens*, *Cynodon dactylon*, Agrostis sp., Lolium sp., *Eleusine indica*, Rottboellia spp., Cenchrus sp. in cultures such as sugar beets, cotton, soybeans, peanuts, peas, sunflower, rape and cabbage, and in perennial cultures, such as fruit plants, vines and plantation cultures.

The compositions according to the present invention can be applied in the pre-germination techniques, but preferably are applied according to the post-germination techniques, and possess in more advantageous manner, indeed at low application amounts from 0.05 up to 5.0 kg active substance per hectare, a good activity.

Of the compounds according to the present invention, distinguishing by an optimum effectiveness of the above-described type are particularly those for which in the Formula Z is 2,4-dichlorophenyl, 4-trifluoromethylphenyl, 4-chlorophenyl, 2-chloro-4-trifluoromethylphenyl, 5-trifluoromethyl-2-pyridyl, 3,5-dichloro-2-pyridyl, 3-chloro-5-trifluoromethyl-2-pyridyl, 6-chloro-2-quinoxalinyl or 6-fluoro-2-quinoxalinyl, and $R_1$ and $R_2$ are the same or different and are each hydrogen, methyl, ethyl, propyl, isopropyl, n-butyl, sec.-butyl, tert.-butyl, 2,2-dimethyl-1-propyl, n-pentyl, n-heptyl, n-octyl, n-decyl, chloromethyl, bromomethyl, fluoroethyl, dichloromethyl, trifluoromethyl, trichloromethyl, methoxymethyl, ethoxymethyl, phenoxymethyl, 4-chlorophenoxymethyl, chloroethyl, bromoethyl, 2-ethoxyethyl, 2-phenoxyethyl, cyclopropyl, cyclopentyl, cyclohexyl, benzyl, 2-phenylethyl, phenyl, 2-chlorophenyl, 3-chlorophenyl, 4-chlorophenyl, 3,4-dichlorophenyl, 4-methoxyphenyl, 4-nitrophenyl or 2,4-dichlorophenyl or together with the C-atom to which they are bonded a cyclopentyl or cyclohexyl group.

Compounds according to the present invention with most outstanding effectiveness are particularly those with which in the general Formula I, $Y_1$, $Y_3$ or $Y_5$ is the group

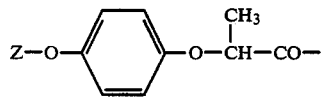

and the pairs $Y_2$ and $Y_3$ as well as $Y_4$ and $Y_5$, or $Y_1$ and $Y_2$ as well as $Y_4$ and $Y_5$, or $Y_1$ and $Y_2$ as well as $Y_3$ and $Y_4$, are the group.

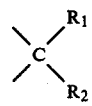

wherein Z, $R_1$ and $R_2$ have the previously given meaning.

The compounds according to the present invention occur as optical isomers, and in some cases also as geometrical isomers. The individual isomers and their mixtures also belong to the subject of the present invention.

The compounds according to the present invention can be used either alone, in mixture with one another, or with other active substances. If necessary, defoliation agents, plant protection agents or pest control agents, indeed according to the desired purpose, can be added to the compositions.

To the extent that a broadening of the activity spectrum is intended, also other biocides can be added. Examples of suitable herbicidally effective mixture partners are those active substances set forth in Weed Abstracts, Vol. 31, No. 7, 1982, under the title "List of common names and abbreviations employed for currently used herbicides and plant growth regulators in Weed Abstracts".

It has moreover been determined that compositions containing the compounds according to the present invention, in mixture with several already known herbicides from Weed Abstracts, such as Phenmedipham, Desmedipham and analogous biscarbamates, provide an increased herbicidal effectiveness.

The subject of the present invention therefore includes, moreover, herbicidal mixtures which are thereby characterized in that they contain at least one compound of the general Formula I in mixture with at least one compound of the general Formula

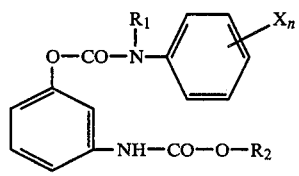

VIII in which
$R_1$ is hydrogen or $C_1$–$C_3$-alkyl,
$R_2$ is $C_1$–$C_3$-alkyl,
X is $C_1$–$C_3$-alkyl, halogen or CN-, and
n is 0, 1, 2 or 3;
in a weight ratio from 1:10 to 10:1. Preferably, the weight ratio is from 1:3 up to 3:1.

As particularly suitable mixture partners of the general Formula VIII, mention may be made of the following known compounds:
methyl-N-(3-(N'-(3'-methylphenyl)-carbamoyloxy)-phenyl)-carbamate, (Phenmedipham)
ethyl-N-(3-(N'-phenylcarbamoyloxy)-phenyl)-carbamate, (Desmedipham) and
isopropyl-N-(2-(N'-ethyl-N'-phenylcarbamoyloxy)phenyl-carbamate.

A most particularly suitable compound of the Formula I which can be used as a mixing partner is the compound 5-O-{2-[4-(5-trifluoromethyl-2-pyridyloxy)-phenoxy]-propionyl}-1,2,:3,4-bis-O-(isopropylidene)-xylite.

The herbicidal effectiveness of these biscarbamates is already known, but they prove under particular conditions to be still in need of improvement, for example for the combating of very resistant dicotyledonousweeds and weed grasses, particularly in cultures of sugar beets and food beets.

In surprising manner the mixtures according to the present invention display a considerably increased effectiveness against such weeds and weed grasses, without the therewith treated beet plants being injured.

The present invention is thus also involved with an advantageous alteration in the herbicidal effectiveness of the mentioned biscarbamates, in that these themselves upon aggravated conditions, such as very high application amounts, do not act harmfully to the beets while simultaneously broadening their activity spectrum to the weed grasses.

The weight ratio of the components in the mixtures according to the present invention should amount to between about 1:10 and 10:1, preferably from 1:3 up to 3:1.

The preferred amount of active substance for selective weed control runs from about 0.5 up to 5.0 kg/ha for the compounds of formula VIII and from about 0.25 up to 5.0 kg/ha for the compounds of formula I.

It is moreover advantageous to add an amount of suitable surface-active substance between 0.25 up to 5.0 kg/ha and other activity strengtheners, such as non-phytotoxic oils. Expediently the active substance according to the present invention or mixtures thereof are employed in the form of preparations such as powders, spray agents, granulates, solutions, emulsions or suspensions, with the addition of liquid and/or solid carrier materials or diluting agents and, if necessary, wetting, adhering, emulsifying and/or dispersing adjuvants. Preferably, they are employed in the form of emulsion concentrates.

Suitable liquid carrier substances include, for example, water, aliphatic and aromatic hydrocarbons such as benzene, toluene, xylene, cyclohexanone, isophorone, dimethyl sulfoxide, dimethyl formamide and, moreover, mineral oil fractions.

Suitable solid carrier substances are mineral earths, for example tonsil, silica gel, talc, kaolin, attaclay, limestone, silicic acid and plant products such as for example meal.

Surface-active substances worthy of mention include, for example, calcium lignin sulfonate, polyoxyethylene-alkylphenol ether, naphthaline sulfonic acids and their salts, phenol sulfonic acids and their salts, formaldehyde condensate, fatty alcohol sulfate as well as substituted benzene sulfonic acids and their salts.

The portion of active substance(s) in the different preparations can vary within broad limits. For example, the compositions can contain about 5 up to 95% by weight active substance, about 95 to 5% by weight liquid or solid carrier material, with or without up to 20% by weight surface-active substance, upon corresponding reduction in the amount of carrier.

The application of the composition can follow in customary manner, for example with water as carrier in spray brew amounts from about 100 to 1,000 liter/ha. A use of the compositions in the so-called low-volume and ultra-low-volume techniques is likewise possible, as well as their application in the form of so-called microgranulates.

By way of example, the following components may be employed for production of the preparations:

A. Spray Powder
(a) 40% by weight  Active Substance
    25% by weight  Clay minerals
    20% by weight  Colloidal Silicic acid
    10% by weight  Cell pitch
    5% by weight   Surface-active substance based upon
                   a mixture of the calcium salt of
                   lignin sulfonic acid with
                   alkylphenolpolyglycolethers -continued

| | | |
|---|---|---|
| (b) | 25% by weight | Active substance |
| | 60% by weight | Kaolin |
| | 10% by weight | Colloidal silicic acid |
| | 5% by weight | Surface-active material based upon the sodium salt of N—methyl-N—oleyl-taurine and the calcium salt of lignin sulfonic acid |
| (c) | 10% by weight | Active substance |
| | 60% by weight | Clay minerals |
| | 15% by weight | Colloidal silicic acid |
| | 10% by weight | Cell pitch |
| | 5% by weight | Surface-active material based upon the sodium salt of N—methyl-N—oleyl-taurine and the calcium salt of lignin sulfonic acid |
| B. Paste | | |
| | 45% by weight | Active substance |
| | 5% by weight | Sodium aluminum silicate |
| | 15% by weight | Cetylpolyglycolether with 8 Mol ethylene oxide |
| | 2% by weight | Spindle oil |
| | 10% by weight | Polyethyleneglycol |
| | 23 parts | Water |
| C. Emulsion Concentrate | | |
| (a) | 25% by weight | Active substance |
| | 15% by weight | Cyclohexanone |
| | 55% by weight | Xylene |
| | 5% by weight | Mixture of nonylphenylpolyoxy-ethylene or calcium dodecylbenzene sulfonate |
| (b) | 10% by weight | Active substance |
| | 6% by weight | Cyclohexanone |
| | 36% by weight | Xylene |
| | 12% by weight | Mixture of nonylphenylpolyoxy-ethylene or calcium dodecylbenzene sulfonate |
| | 36% by weight | Mineral oil with high paraffin content |

The new compounds according to the present invention of general Formula I can be produced, for example, by reacting
(a) compounds of the general Formula

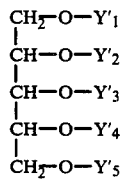
II in which one of substituents Y' is hydrogen and pairs of other substituents Y' represent the group

with compounds of the Formula

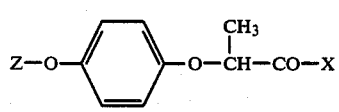
III or
(b) compounds of the Formula

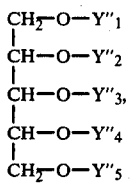
IV in which one of substituents Y'' is the group

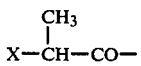

and pairs of other substituents Y' are the group

with compounds of the Formula

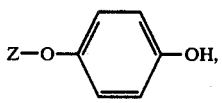
V (c) compounds of the Formula

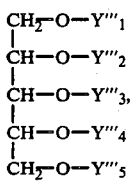
VI in which one of substituents Y''' is the group

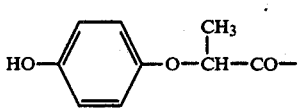

and pairs of other substituents Y''' are the groups

with compounds of the Formula

Z—X      VII if necessary in the presence of acid-binding agents and/or catalysts, wherein Z, $R_1$ and $R_2$ have the above given meaning and X is halogen, preferably chlorine or bromine.

The duration of reaction amounts to from 1 to 72 hours. As a rule the reactions follow at normal pressure or slight excess pressure. For synthesis of the compounds according to the present invention the reactants are employed in about equimolar amounts. Suitable reaction media include solvents inert with respect to the reactants. The choice of solvent or suspension agents is directed according to the employment of corresponding alkyl or acyl halogenide, and the employed acid acceptors. As solvent or suspension agent mention may be made by way of example of aliphatic and aromatic hydrocarbons, such as petroleum ether, cyclohexane, hexane, heptane, benzene, toluene, xylene; halogenated hydrocarbons such as methylene chloride, ethylene chloride, chlorobenzene, chloroform, carbon tetrachloride, tetrachloroethylene; ethers such as diethylether, diisopropylether, anisol, dioxan, tetrahydrofuran; carboxylic acid nitriles such as acetonitrile, propionitrile; carboxylic acid amides such as dimethylformamide; dimethylsulfoxide; ketones such as acetone, diethylketone, methylethylketone; alcohols such as methanol, ethanol, propanol, butanol and mixtures of such solvents with one another. In several cases also the reaction partners themselves can serve as solvent.

As acid acceptors, suitable are organic bases such as for example triethylamine, trimethylamine, N,N-dimethylaniline, pyridine and pyridine bases (4-dimethylaminopyridine) or organic bases such as oxides, hydroxides, carbonates, hydrogen carbonates and alcoholates of alkali and earth alkali metals, as well as alkali salts of carboxylic acids, for example KOH, NaOH, $Na_2CO_3$ and $CH_3COONa$.

Liquid bases such as pyridine can simultaneously be employed as solvent. Arising hydrogen halide can in many cases also be removed from the reaction mixture by means of a throughput of inert gas, for example nitrogen, or by adsorption on molecular sieves.

The presence of a reaction catalyst can be of advantage. As catalyst, suitable examples include potassium iodide and onium compounds, such as quaternary ammonium, phosphonium and arsonium compounds, as well as sulfonium compounds. Likewise suitable are polyglycolethers, in particular cyclical, such as for example 18-crown-6, and tertiary amines such as, for example, tributylamine. Preferred compounds are quaternary ammonium compounds, such as for example benzyltriethylammonium chloride and tetrabutylammonium bromide.

The compounds according to the present invention prepared according to the above mentioned processes can be isolated from the reaction mixture by customary techniques, for example by distilling off of the employed solvent at normal or decreased pressure, by precipitation with water or by extraction. An elevated degree of purity can as a rule be obtained by means of column chromatographical purification as well as by fractionating distillation.

The compounds according to the present invention represent as a rule nearly colorless and odorless liquids, which are difficultly soluble in water, conditionally soluble in aliphatic hydrocarbons such as petroleum ether, hexane, pentane and cyclohexane, well soluble in halogenated hydrocarbons such as chloroform, methylene chloride and carbon tetrachlcoride, aromatic hydrocarbons such as benzene, toluene and xylene, ethers such as diethylether, tetrahydrofuran and dioxan, carboxylic acid nitriles such as acetonitrile, ketones such as acetone, alcohols such as methanol and ethanol, carboxylic acid amides such as dimethylformamide and sulfoxide such as dimethylsulfoxide.

The compounds of the Formula I possess always in the group

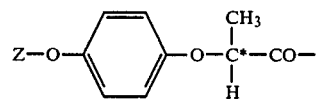

an asymmetrical carbon atom C*. Upon synthesis the active substance in normal manner is produced as a racemic mixture and can in known manner, for example by fractionating crystallization, be split into the optically opposite form.

The synthesis of an optically pure compound of Formula I is possible when one, upon its production, proceeds from an optically clear 2-halogen propionic acid. The optically opposite forms of I possess distinguishing biological activities. As a rule, the D-form is more herbicidally effective.

The starting compounds for production of the compounds according to the present invention are known per se or can be prepared according to known processes.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

The following Examples illustrate the production of the pentite ester according to the present invention.

EXAMPLE 1

5-O-{2-[4-(5-trifluoromethyl-2-pyridyloxy)-phenoxy]-propionyl}-1,2:3,4-bis-O-(isopropylidene)-xylite 7.0 g (0.03 Mol) 1,2:3,4-bis-O-(isopropylidene)-xylite are provided in 50 ml methylene chloride and, at 20° C., reacted with 8.4 ml (0.06 Mol) triethylamine. Subsequently there is added dropwise a solution of 10.4 g (0.03 Mol) 2-4-(5-trifluoromethyl-2-pyridyloxy)-phenoxy-propionic acid chloride in 100 ml methylene chloride, under ice cooling at 20° C. The reaction mixture is then after-stirred for 1 hour at room temperature. The reaction mixture is compressed to dryness and subsequently the residue is withdrawn with 200 ml ethyl acetate. The ethyl acetate extract is first washed with water, and then with saturated potassium carbonate solution. It is then dried across magnesium sulfate and subsequently filtered. After driving off of the solvent the remaining oil is dried at 50° C./0.1 Torr.

Yield: 13.1 g = 80.7% of theoretical amounts.

$n_D^{20}$: 1.4907.

DC: flowing agent=ethyl acetate; $R_f$-value=0.67.

Analysis: calculated: C 57.66%; H 5.58%; N 2.59%; F 10.53%. found: 57.76%; 5.88%; 2.37%; 9.80%.

In analogous manner the following compounds according to the present invention are produced:

| Example No. | Name of Compound | Physical Constant |
|---|---|---|
| 2 | 1-O—{2-[4-(5-trifluoromethyl-2-pyridyloxy)-phenoxy]-propionyl} 2,3:4,5-bis-O—(isopropylidene)-D-arabite | $n_D^{20}$ 1.4938 |
| 3 | 3-O—{2-[4-(5-trifluoromethyl-2- | $n_D^{20}$ 1.4942 |

-continued

| Example No. | Name of Compound | Physical Constant |
|---|---|---|
|  | pyridyloxy)-phenoxy]-propionyl}-1,2:4,5-bis-O—(isopropylidene)-adonite |  |
| 4 | 5-O—{2-[4-(5-trifluoromethyl-2-pyridyloxy)-phenoxy]-propionyl}-1,2:3,4-bis-O—(phenyl-methylene)-xylite | MP: 150–160° C. |
| 5 | 5-O—{2-[4-(5-trifluoromethyl-2-pyridyloxy)-phenoxy]-propionyl}-1,2:3,4-bis-O—(4-chloro-phenylmethylene)-xylite | MP: 142–143° C. |
| 6 | 5-O—{2-[4-(5-trifluoromethyl-2-pyridyloxy)-phenoxy]-propionyl}-1,2:3,4-bis-O—(methyl-methylene)-xylite | MP: 48–49° C. |
| 7 | 5-O—{2-[4-(5-trifluoromethyl-2-pyridyloxy)-phenoxy]-propionyl}-1,2:3,4-bis-O—(methyl-octyl-methylene)-xylite | $n_D^{20}$ 1.4849 |
| 8 | 5-O—{2-[4-(5-trifluoromethyl-2-pyridyloxy)-phenoxy]-propionyl}-1,2:3,4-bis-O—(chloro-methyl-methylene)-xylite | Oil |
| 9 | 5-O—{2-[4-(2,4-dichlorophenoxy)-phenoxy]-propionyl}-1,2:3,4-bis-O—(isopropylidene)-xylite | $n_D^{20}$ 1.5183 |
| 10 | 5-O—{2-[4-(4-trifluoromethyl-phenoxy)-phenoxy]-propionyl}-1,2:3,4-bis-O—(isopropylidene)xylite | Oil |
| 11 | 5-O—{2-[4-(4-chlorophenoxy)-phenoxy]-propionyl}-1,2:3,4-bis-O—(isopropylidene)-xylite | Oil |
| 12 | 5-O—{2-[4-(2-chloro-4-trifluoromethylphenoxy)-phenoxy]-propionyl}-1,2:3,4-bis-O—(isopropylidene)-xylite | Oil |
| 13 | 5-O—{2-[4-(3,5-dichloro-2-pyridyloxy)-phenoxy]-propionyl}-1,2:3,4-bis-O—(isopropylidene)-xylite | Oil |
| 14 | 5-O—{2-[4-(3-chloro-5-trifluoromethyl-2-pyridyloxy)-phenoxy]-propionyl}-1,2:3,4-bis-O—(isopropylidene)-xylite | Oil |
| 15 | 5-O—{2-[4-(6-chloro-2-quinoxalinyloxy)-phenoxy]-propionyl}-1,2:3,4-bis-O—(isopropylidene)-xylite | Oil |
| 16 | 5-O—{2-[4-(6-fluoro-2-quinoxalinyloxy)-phenoxy]-propionyl}-1,2:3,4-bis-O—(isopropylidene)-xylite | Oil |
|  | 5-O—{2-[4-(5-trifluoromethyl-2-pyridyloxy)-phenoxy]-propionyl}-1,2:3,4-bis-O—(ethylmethyl-methylene)-xylite | $n_D^{20}$ 1.4939 |
|  | 5-O—{2-[4-(5-trifluoromethyl-2-pyridyloxy)-phenoxy]-propionyl}-1,2:3,4-bis-O—(diethylmethylene)-xylite | $n_D^{20}$ 1.4924 |
|  | 5-O—{2-[4-(3-chloro-5-trifluoromethyl-2-pyridyloxy)-phenoxy]-propionyl}-1,2:3,4-bis-O—(isopropylidene)-xylite | $n_D^{20}$ 1.4973 |

The following Examples illustrate use possibilities for the compounds of the invention and their mixtures, which follow the form of the above given preparation.

EXAMPLE 17

In a greenhouse the compounds according to the present invention set forth in the following Table are sprayed in an application amount of 5.0 kg active substance per hectare emulsified in 500 liter water per hectare, onto Setaria and Lolium as test plants, in both pre- and post-germination techniques. 3 weeks after the treatment the treatment results are classified, whereby 0 = no activity, and
4 = destruction of the plants As is evident from the following Table, as a rule the test plants are destroyed.

| Compounds According to the Invention | Pre-germination | | Post-germination | |
|---|---|---|---|---|
|  | Setaria | Lolium | Setaria | Lolium |
| 5-O—{2-[4-(5-trifluoromethyl-2-pyridyloxy)-phenoxy]-propionyl}-1,2:3,4-bis-O—(isopropylidene)-xylite | 4 | 4 | 4 | 4 |
| 1-O—{2-[4-(5-trifluoromethyl-2-pyridyloxy)-phenoxy]-propionyl}-2,3:4,5-bis-O—(isopropylidene)-D-arabite | 4 | 4 | 4 | 4 |
| 3-O—{2-[4-(5-trifluoromethyl-2-pyridyloxy)-phenoxy]-propionyl}-1,2:4,5-bis-O—(isopropylidene)-adonite | 4 | 4 | 4 | 4 |
| 5-O—{2-[4-(5-trifluoromethyl-2-pyridyloxy)-phenoxy]-propionyl}-1,2:3,4-bis-O—(ethylmethylmethylene)-xylite | 4 | 4 | 4 | 4 |
| 5-O—{2-[4-(5-trifluoromethyl-2-pyridyloxy)-phenoxy]-propionyl}-1,2:3,4-bis-O—(diethylmethylene)-xylite | 4 | 4 | 4 | 4 |
| 5-O—{2-[4-(3-chloro-5-trifluoromethyl-2-pyridyloxy)-phenoxy]-propionyl}-1,2:3,4-bis-O—(isopropylidene)-xylite | 4 | 4 | 4 | 4 |

EXAMPLE 18

In a greenhouse the plants listed in the following Table are treated after germination with the listed compound in an application amount of 0.1 kg active substance/ha. For this purpose the compound is sprayed as an emulsion with 500 liters water/ha, uniformly over the plants. 3 weeks after the treatment, it is evident that the compounds according to the present invention display a high selectivity with excellent activity against the weeds.

14 days after the treatment, the results of the treatment are classified according to the scheme from 0 up to 10, whereby 0 means total destruction and 10 means no activity.

| Compound According to the Invention | Hordeum | Avena | Sorghum | Setaria | Oryza | Alopecurus | Digitaria | Sugar beets | Soy-beans | Sun Flowers | Potatoes | Rape |
|---|---|---|---|---|---|---|---|---|---|---|---|---|
| 5-O—{2-[4-(5-trifluoromethyl-2- | 0 | 0 | 0 | 0 | 0 | 0 | 0 | 10 | 10 | 10 | 10 | 10 |

| Compound According to the Invention | Hordeum | Avena | Sorghum | Setaria | Oryza | Alopecurus | Digitaria | Sugar beets | Soybeans | Sun Flowers | Potatoes | Rape |
|---|---|---|---|---|---|---|---|---|---|---|---|---|
| pyridyloxy)-phenoxy]-propionyl}-1,2:3,4-bis-O—(isopropylidene)-xylite | | | | | | | | | | | | |

EXAMPLE 19

The compounds set forth in the following Table and their mixtures are applied to a stand of weeds in the given application amounts. The compounds are for this purpose emulsified in 500 l water/ha and uniformly sprayed over the plants. For the first 8 days after the treatment, the plants are exposed during the day to strong solar radiation (100,000 lux) and high temperature (up to 40° C.). The stand of weeds is composed of the broad-leaf types *Stellaria media, Matricaria chamomilla, Centaurea cyanus, Galium aparine, Chrysanthemum segetum, Ipomea purpurea, Sinapis alba* and the weed grasses *Avena fatua, Alopecurus myosuroides,* Echinochloa c.g., *Setaria italica, Digitaria sanguinalis, Sorghum halepense, Agropyron repens* and *Cynodon dactylon.*

14 days after the treatment, the results of the treatment are classified according to the scheme 0 through 10, whereby 0 signifies total destruction and 10 means no effectivness.

As is evident from the following Table, the mixture according to the present invention acts better than the individual components.

| Components | Application Amounts kg/ha | Sugar beets | Zea mays | Hordeum | Avena | Sorghum | Poa | Agropyron repens | Cynodon dactylon | Digitaria | Setaria | Echinochloa | Alopecurus | Sinapis | Stellaria |
|---|---|---|---|---|---|---|---|---|---|---|---|---|---|---|---|
| 5-O—{2-[4-(5-triflouro-methyl-2-pyridyloxy)-phenoxy]-propionyl}-1,2:3,4-bis-O—(isopropylidene)-xylite (I) | 0.24 | 10 | 0 | 0 | 0 | 0 | 2 | 0 | 0 | 0 | 0 | 0 | 0 | 10 | 10 |
| Phenmedipham (II) | 0.72 | 10 | 7 | 6 | 5 | 8 | 3 | 10 | 10 | 8 | 8 | 7 | 6 | 0 | 0 |
| I + II | 0.72 + 0.24 | 10 | 0 | 0 | 0 | 0 | 0 | 0 | 0 | 0 | 0 | 0 | 0 | 0 | 0 | sprayed uniformly over the plants as an emulsion with 500 liters water/ha. 3 weeks after the treatment the results of the treatment are classified, whereby 0=destruction of the plants, and
10=no injury.

As is evident from the Table, the mixture according to the present invention acts strongly against numerous problem weeds, with complete harmlessness to the sugar beets.

| Components | Application Amounts kg/ha | Sugar beets | Broad-leaf weeds | Grass weeds |
|---|---|---|---|---|
| 5-O—{2-[4-(5-trifluoro-methyl-2-pyridyloxy)-phenoxy]-propionyl}-1,2:3,4-bis-O—(isopropylidene)-xylite (I) | 1 | 10 | 10 | 0 |
| | 3 | 10 | 10 | 0 |
| Phenmedipham (II) | 1 | 9 | 0 | 10 |
| | 3 | 5 | 0 | 10 |
| I + II | 1 | 10 | 0 | 0 |
| | 3 | 10 | 0 | 0 |

EXAMPLE 20

In a greenhouse the plants listed in the following Table are treated, after germination, with the listed components or their mixtures. To this end, they are It will be understood that each of the elements described above, or two or more together, may also find a useful application in other types of herbicide differing from the types described above.

While the invention has been illustrated and described as embodied in 2-phenoxy propionic acid derivatives of pentite, process for the production of these compounds as well as compositions containing the same having herbicidal effectiveness, it is not intended to be limited to the details set forth, since various modificationss and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. 2-Phenoxy propionic acid derivatives of pentites of the formula:

$$\begin{array}{l} CH_2-O-Y_1 \\ | \\ CH-O-Y_2 \\ | \\ CH-O-Y_3 \\ | \\ CH-O-Y_4 \\ | \\ CH_2-O-Y_5 \end{array}$$

wherein, one substituent of the group consisting of Y₁, Y₃ and Y₅, is the group

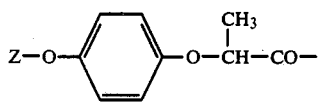

and pairs of other substituents Y are the radicals from the group consisting of Y₂/Y₃ and Y₄/Y₅, Y₁/Y₂ and Y₄/Y₅, and Y₁/Y₂ and Y₃/Y₄, are the group

wherein,
Z represents a member selected from the group consisting of 5-trifluoromethyl-2-pyridyl, 3-chloro-5-trifluoromethyl-2-pyridyl and 3,5-dichloro-2-pyridyl;
R₁ represents a member selected from the group consisting of hydrogen, methyl and ethyl; and
R₂ represents a member selected from the group consisting of methyl, ethyl, octyl, chloromethyl, phenyl and 4-chlorophenyl.

2. The compound according to claim 1, which is 5-O-{2-[4-(5-trifluoromethyl-2-pyridyloxy)-phenoxy]-propionyl}-1,2:3,4-bis-O-(isopropylidene)-adonite.

3. The compound according to claim 1, which is 1-O-{2-[4-(5-trifluoromethyl-2-pyridyloxy)-phenoxy]-propionyl}-2,3:4,5-bis-O-(isopropylidene)-D-arabite.

4. The compound according to claim 1, which is 3-O-{2-[4-(5-trifluoromethyl-2-pyridyloxy)-phenoxy]-propionyl}-1,2:4,5-bis-O-(isopropylidene)-adonite.

5. The compound according to claim 1, which is 5-O-{2-[4-(5-trifluoromethyl-2-pyridyloxy)-phenoxy]-propionyl}-1,2:3,4-bis-O-(phenylmethylene)-xylite.

6. The compound according to claim 1, which is 5-O-{2-[4-(5-trifluoromethyl-2-pyridyloxy)-phenoxy]-propionyl}-1,2:3,4-bis-O-(4-chlorophenylmethylene)-xylite.

7. The compound according to claim 1, which is 5-O-{2-[4-(5-trifluoromethyl-2-pyridyloxy)-phenoxy]-propionyl}-1,2:3,4-bis-O-(methylmethylene)-xylite.

8. The compound according to claim 1, which is 5-O-{2-[4-(5-trifluoromethyl-2-pyridyloxy)-phenoxy]-propionyl}-1,2:3,4-bis-O-(methyloctylmethylene)-xylite.

9. The compound according to claim 1, which is 5-O-{2-[4-(5-trifluoromethyl-2-pyridyloxy)-phenoxy]-propionyl}-1,2:3,4-bis-O-(chloromethylmethylene)-xylite.

10. The compound according to claim 1, which is 5-O-{2-[4-(3,5-dichloro-2-pyridyloxy)-phenoxy]-propionyl}-1,2:3,4-bis-O-(isopropylidene)-xylite.

11. The compound according to claim 1, which is 5-O-{2-[4-(3-chloro-5-trifluoromethyl-2-pyridyloxy)-phenoxy]-propionyl}-1,2:3,4-bis-O-(isopropylidene)-xylite.

12. The compound according to claim 1, which is 5-O-2-[4-(5-trifluoromethyl-2-pyridyloxy)-phenoxy]-propionyl-1,2:3,4-bis-O-(ethylmethyl-methylene)-xylite.

13. The compound of claim 1, which is 5-O-2-[4-(5-trifluoromethyl-2-pyridyloxy)-phenoxy]-propionyl-1,2:3,4-bis-O-(diethylmethylene)-xylite.

14. A herbicidal composition comprising an effective amount of a 2-phenoxy propionic acid derivative of pentite selected from the group consisting of:
5-O-2-[4-(5-trifluoromethyl-2-pyridyloxy)-phenoxy]-propionyl-1,2:3,4-bis-O-(isopropylidene)-xylite;
1-O-2-[4-(5-trifluoromethyl-2-pyridyloxy)-phenoxy]-propionyl-2,3:4,5-bis-O-(isopropylidene)-D-arabite;
3-O-2-[4-5-trifluoromethyl-2-pyridyloxy)-phenoxy]-propionyl-1,2:4,5-bis-O-(isopropylidene)-adonite;
5-O-2-[4-(5-trifluoromethyl-2-pyridyloxy)-phenoxy]-propionyl-1,2:3,4-bis-O-(phenylmethylene)-xylite;
5-O-2-[4-(5-trifluoromethyl-2-pyridyloxy)-phenoxy]-propionyl-1,2:3,4-bis-O-(4-chlorophenylmethylene)-xylite;
5-O-2-[4-(5-trifluoromethyl-2-pyridyloxy)-phenoxy]-propionyl-1,2:3,4-bis-O-(methylmethylene)-xylite;
5-O-2-[4-(5-trifluoromethyl-2-pyridyloxy)-phenoxy]-propionyl-1,2:3,4-bis-O-(methyloctylmethylene)-xylite;
5-O-2-[4-(5-trifluoromethyl-2-pyridyloxy)-phenoxy]-propionyl-1,2:3,4-bis-O-(chloromethylmethylene)-xylite;
5-O-2-[4-(2,4-dichlorophenoxy)-phenoxy]-propionyl-1,2:3,4-bis-O-(isopropylodene)-xylite;
5-O-{2-[4-(5-trifluoromethyl-2-pyridyloxy)-phenoxy]-propionyl}-1,2:3,4-bis-O-(ethylmethyl-methylene)-xylite;
5-O-{2-[4-(5-trifluoromethyl-2-pyridyloxy)-phenoxy]-propionyl}-1,2:3,4-bis-O-(diethylmethylene)-xylite;
5-O-2-[4-(3,5-dichloro-2-pyridyloxy)-phenoxy]-propionyl-1,2:3,4-bis-O-(isopropylidene)-xylite;
5-O-2-[4-(3-chloro-5-trifluoromethyl-2-pyridyloxy)-phenoxy]-propionyl-1,2:3,4-bis-O-(isopropylidene)-xylite; and
together with suitable solid or liquid carriers therefore.

* * * * *